United States Patent
Stamler

(10) Patent No.: US 7,540,860 B2
(45) Date of Patent: Jun. 2, 2009

(54) WOUND IRRIGATION SPLASHBACK SHIELD

(76) Inventor: Keith Stamler, P.O. Box 4375, Palos Verdes Penninsula, CA (US) 90274

( * ) Notice: Subject to any disclaimer, the term of this patent is extended or adjusted under 35 U.S.C. 154(b) by 627 days.

(21) Appl. No.: 11/337,285

(22) Filed: Jan. 23, 2006

(65) Prior Publication Data

US 2007/0173773 A1 Jul. 26, 2007

(51) Int. Cl.
*A61M 37/00* (2006.01)
(52) U.S. Cl. .................................. 604/268
(58) Field of Classification Search ........... 604/187, 604/192, 268, 289, 296, 300, 312, 313, 315, 604/316, 35, 36, 119, 263, 116, 543; 128/917, 128/919, 846, 847, 849; 433/80, 116
See application file for complete search history.

(56) References Cited

U.S. PATENT DOCUMENTS

| | | | |
|---|---|---|---|
| 3,896,810 A * | 7/1975 | Akiyama | ............... 604/117 |
| 4,516,968 A | 5/1985 | Marshall et al. | |
| 4,769,003 A | 9/1988 | Stamler | |
| D307,474 S | 4/1990 | Cook | |
| D345,016 S | 3/1994 | Stamler | |
| 5,496,290 A | 3/1996 | Ackerman | |
| 5,735,833 A | 4/1998 | Olson | |
| 5,842,863 A | 12/1998 | Bruns et al. | |
| 5,860,947 A | 1/1999 | Stamler | |
| 5,941,859 A * | 8/1999 | Lerman | ............... 604/289 |
| 6,200,291 B1 | 3/2001 | Di Pietro | |
| 6,210,381 B1 | 4/2001 | Morse | |
| 6,293,929 B1 | 9/2001 | Smith et al. | |
| 6,402,724 B1 * | 6/2002 | Smith et al. | ............... 604/289 |
| 6,485,452 B1 | 11/2002 | French et al. | |
| 6,558,344 B2 | 5/2003 | McKinnon et al. | |
| 6,632,204 B2 | 10/2003 | Guldfeldt et al. | |
| 6,811,547 B2 | 11/2004 | Wilkinson | |
| D507,833 S | 7/2005 | Coss | |

OTHER PUBLICATIONS

Zero Wet Splashield Web page Oct. 31, 2005.
Bionix Igloo Wound Irrigator Web page Dec. 22, 2005.
Busse Wound Irrigation Web page Dec. 22, 2005.

* cited by examiner

*Primary Examiner*—Manuel A Mendez
(74) *Attorney, Agent, or Firm*—Robert J. Lauson; Lauson & Tarver LLP

(57) ABSTRACT

A splashback shield for attachment to a syringe for wound irrigation includes a generally dome-shaped shield with a conduit or tunnel through the top that narrows to form a nozzle as it extends substantially inside the shield. A number of air vents or passageways surround the conduit so when submerging and re-filling the syringe with irrigant with the shield attached any air trapped inside the shield escapes rather than drawn into the syringe. The air vents are preferably elongate tubular passageways that narrow exiting the shield, facilitating air escaping but the irrigant mixed with any blood and contamination tends not to pass through the vents. The device is an improvement over the conventional Zerowet® Splashield® product.

21 Claims, 4 Drawing Sheets

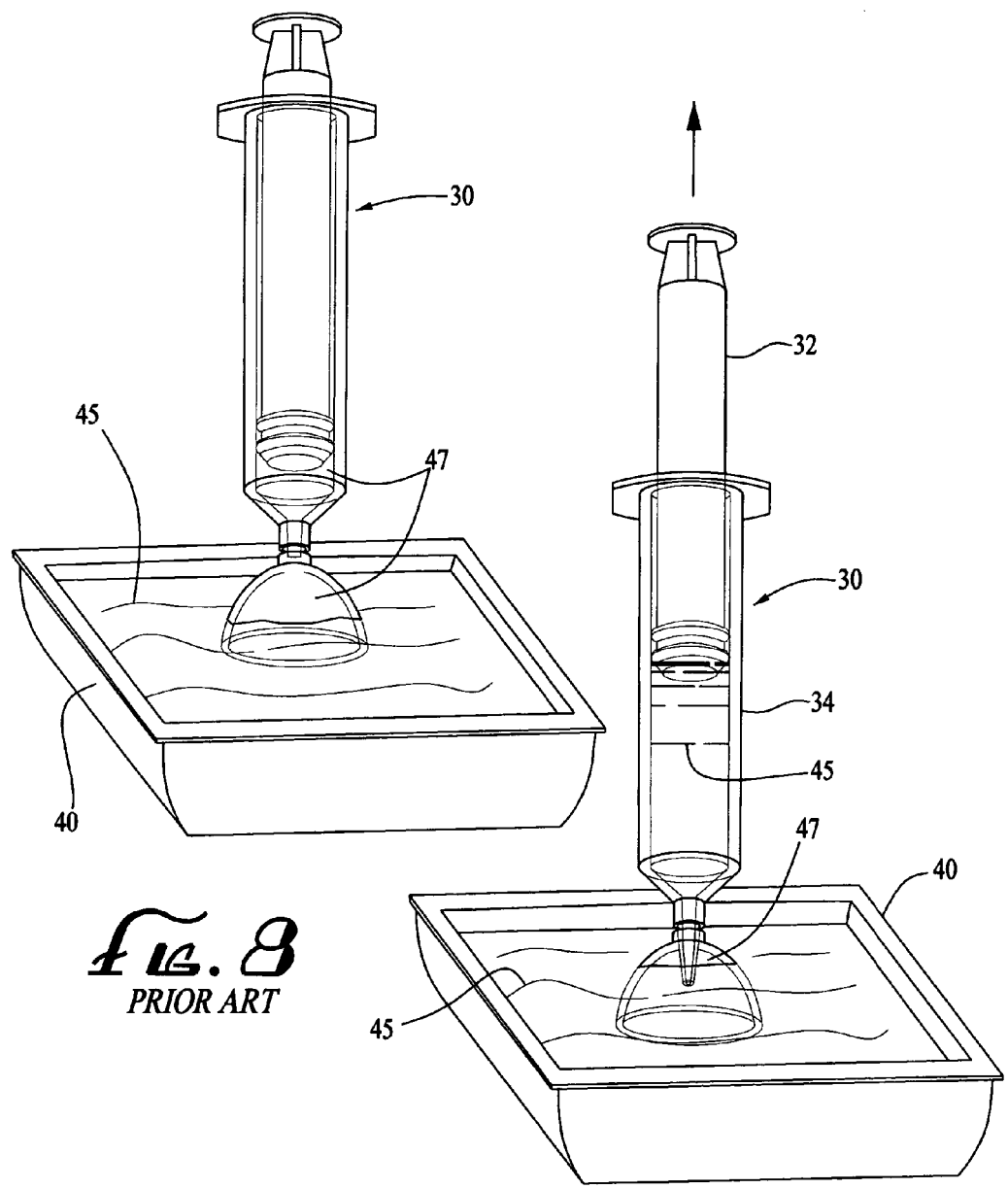

WOUND IRRIGATION SPLASHBACK SHIELD

BACKGROUND OF THE INVENTION

1. Field of the Invention

The present invention relates to medical devices for irrigation of wounds, and in particular to an improved splashback shield that enables a user to quickly, safely and economically flush a wound with multiple volumes of irrigant.

2. Description of the Related Art

Not so long ago there were no such things as sharps containers or needlestick exposure protocols. Wound irrigation was performed using a syringe and a needle or an IV catheter. The splash was a nuisance as were accidental needlesticks, but no one was really concerned about protection from deadly infectious diseases. Then, as time went by, more unlucky individuals became infected with HIV and hepatitis from occupational exposures to seropositive blood.

In 1990, the Zerowet® Splashield® product was introduced to emergency physicians at the SAEM (Society for Academic Emergency Medicine) meeting in Minneapolis. See prior art FIG. 1 of this application. The response was immediate and overwhelming. Since then, the Zerowet® Splashield® product 10 has become the preferred wound irrigation safety device of emergency physicians, nurses, NP's and PA's all across the country. In fact, it's found in nearly two of every three emergency departments nationally, and of course used internationally as well as in offices, clinics, prisons, military bases, convalescent homes and other settings too. The Zerowet® Splashield® was the subject of the Stamler U.S. Pat. Nos. 4,769,003 and Des. 344,133.

The Zerowet®& Splashield®as described in the Stamler patents and when properly used completely eliminates splash, while providing the optimal irrigation pressure recommended by nearly all textbooks covering the subject. In fact, many such textbooks recommend the Zerowet® Splashield® product by name. The cost of a Zerowet® Splashield® is less than the price of a typical IV catheter. Although some practitioners who think squeezing a bottle of saline works as well, studies show that this method generates only about 10% of the recommended pressure; the literature says "[d]on't do it!"

Over the years others have added "frills" in attempts to improve on the performance of the original Zerowet® Splashield® without any real success. Special egg shapes, carefully planned fluid impact angles, directional arrows, a myriad of exhaust ports and one (the Bionix® Igloo® Wound Irrigator) with a purported improved, multi-hole "Shower of Power" (but that product was later quietly pulled from the market, as they went back to a single hole design as originally introduced in 1990 by Dr. Stamler). See, e.g. the Morse U.S. Pat. No. 6,210,381 and the McKinnon U.S. Pat. No. 6,558,344. Note that Bionix, Westmed, Ethox and Busse companies are all licensees of the Stamler '003 patent.

In 1999 U.S. Pat. No. 5,860,947 was awarded to Stamler for a wound irrigation device 20 featuring a two-way check valve 22 with a short fill stem 24 to be installed between the splashback shield 10 and the three-ring "control" syringe 30. See prior art FIG. 2 of this application. This device, commercialized and known as the Klenzalac® wound irrigation system 20 is for treatment of larger, complex or heavily contaminated wounds including bites, crash injuries and open fractures. It allows irrigant 45 from a nearby basin 40 to be repeatedly and conveniently drawn directly into the syringe 30 and then dispensed through and inside the splashback shield 10.

When using the conventional prior art splashback shield 10 (FIG. 1) it is typically necessary to fill and refill the syringe at least a couple of times to completely and effectively irrigate average wounds. In doing so it is necessary to remove the splashback shield 10 while drawing in irrigant 45, or else air trapped under the shield 10 will initially be pulled into the syringe before the irrigant 45 (reducing the volume of irrigant to be dispensed). See prior art FIG. 8. The shield 10 is then replaced to irrigate the wound. While the Klenzalac® product 20 disclosed in the Stamler '947 patent is advantageous in avoiding this problem, it is extra equipment at an additional cost.

OBJECTS OF THE INVENTION

Accordingly, it is an object of the present invention to provide an improved splashback shield for use in wound irrigation that allows repeated filling of the syringe and dispensing of irrigant (or injectant) without detaching the shield from the syringe;

It is a further object of the present invention to provide an improved splashback shield that may be conveniently used for treatment of not only routine wounds, but also large, complex or heavily contaminated wounds instead of using other additional equipment such as the Kenzalac® product;

It is a further object of the present invention to provide an improved splashback shield that still completely eliminates splash and generates the optimal pressure as does the original Zerowet® Splashield® product;

It is a still further object of the present invention to provide an improved splashback shield that provides optimum performance in terms of air not being sucked into the syringe or trapped in the top of the splashback shield when refilling the syringe;

It is a still further object of the present invention to provide an improved splashback shield with the optimum nozzle design with respect to refilling the syringe even from a shallow basin, and providing substantial flow of irrigant to and from the syringe;

It is a still further object of the present invention to provide an improved splashback shield with air vents that efficiently release trapped air while inhibiting any irrigant or blood escape;

It is a still further object of the present invention to provide an improved splashback shield that minimizes clinging of irrigant to any part of the shield; and, Finally, it is a further object of the present invention to provide an improved splashback shield that is simple and inexpensive to manufacture as has been the case with the original Zerowet® Splashield® product.

These and other objects and advantages will become apparent upon reading the following detailed description and upon reference to the accompanying drawings.

SUMMARY OF THE INVENTION

An improved splashback shield for attachment to a syringe for wound irrigation includes a generally see-through and hollow shield of a defined three-dimensional shape. A conduit goes through the outer surface of the shield near the top and is designed to interface with the syringe, and narrows as it extends into the shield. There are further a number of air vent(s) through the shield near the conduit or the top of the shield. Advantageously, when submerging and re-filling the syringe with irrigant with the shield attached, any air trapped inside the shield is able to escape rather than being drawn into the syringe.

The shield is preferably dome shaped although many other shapes are possible (e.g. a truncated cone, a dome-like shape that is oval at the bottom, etc.). The general dome shape best facilitates draining of irrigant from the shield providing better visibility of the wound as it is irrigated. Additionally, although the preferred embodiment has substantial height compared to its width, other less tall or flatter-shaped shields may perform satisfactorily. Optionally, one or more drain holes, cut-outs or scalloping (not shown) may be provided in the lower portion of the shield along the bottom edge to allow draining of spent irrigant from inside the shield. The conduit is preferably located at the very top of the shield and oriented vertically to be approximately perpendicular to the wound when in use, although the conduit may be otherwise located in the top portion of the shield and as desired at an angle to the wound (not shown). See, e.g., U.S. Pat. No. 6,210,381.

The conduit preferably extends a substantial distance through the inner surface and into the hollow shield, preferably below the air vents so that any trapped air (not forced outside the shield through the vent holes by a shallow level of irrigant as the syringe is submerged) cannot be drawn into the syringe. The conduit preferably widens at the very bottom to form a flared extension, however, to facilitate rapid flow of fluid therethrough when re-filling the syringe. Optionally, the conduit may be recessed into the splashback shield as shown in U.S. Pat. No. 6,558,344

The air vents preferably narrow and extend a substantial distance above the inner surface of the shield and are preferably elongate tubular passageways through the shield, such that they allow air to escape but the irrigant tends not to pass through the vents. These tubular passageways to vent air from inside the shield are preferably located immediately next to and around the conduit for the irrigant.

Alternatively stated, the present invention may also be summarized as a medical device for containing reflected fluids when an injectant is directed at a wounded area of the human body, while at the same time allowing monitoring of the direction and flow of the injectant. The device is for use with injection means for manually filling and directing the injectant under pressure (e.g. a syringe). The device includes a transparent or translucent cup-shaped means (e.g. a concave shield) for covering the wound with the outer rim placed on and around (or near) the area of the wound.

Tunnel means in the device forms a nozzle (preferably extending a substantial distance inside the cup-shaped means) for increasing the pressure and directing the flow of the injectant inside the cup-shaped means. Venting means (preferably one or more narrowing, upwardly extending passageway(s) located near the injectant tunnel means or near the top of the cup-shaped means) in the upper surface of the cup-shaped means allow air to escape from inside while still containing the injectant mixed with any blood droplets, contamination, etc.

In using this device the injectant is refillable without detaching the cup-shaped means from the injection means, and thus the device is more quickly and conveniently repeatedly used to irrigate all wounds including those which are larger, complex or heavily contaminated. These and other features and advantages of the present invention will become apparent from the following detailed description of a preferred embodiment which, taken in conjunction with the accompanying drawings, illustrates by way of example the principles of the invention.

BRIEF DESCRIPTION OF THE SEVERAL VIEWS OF THE DRAWINGS

FIG. 8 is a perspective view showing the prior art Zerowet® Splashield® product in use during re-filling of the syringe; and, FIG. 9 is perspective view showing the improved splashback shield in use during re-filling of the syringe.

LISTING OF REFERENCE NUMERALS FOR THE PREFERRED EMBODIMENT

| | |
|---|---|
| Zerowet ® Splashield ® product (prior art) | 10 |
| Klenzalac ® product (prior art) | 20 |
| two-way check valve | 22 |
| short fill stem | 24 |
| syringe | 30 |
| basin | 40 |
| irrigant or injectant | 45 |
| improved splashback shield | 50 |
| dome or cup-shaped shield | 52 |
| conduit or tunnel | 54 |
| irrigant nozzle | 56 |
| air vents or passageways | 58 |
| flared extension | 60 |
| step or flat area | 62 |
| shoulder | 64 |
| cupola | 66 |

DESCRIPTION OF THE PREFERRED EMBODIMENT(S)

Figure 1:
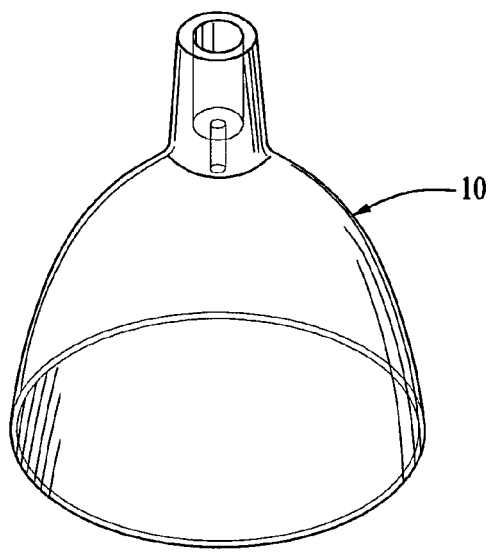
FIG. 1 is a perspective view of the prior art Zerowet® Splashield® product disclosed in the Stamler patents.
Figure 2:
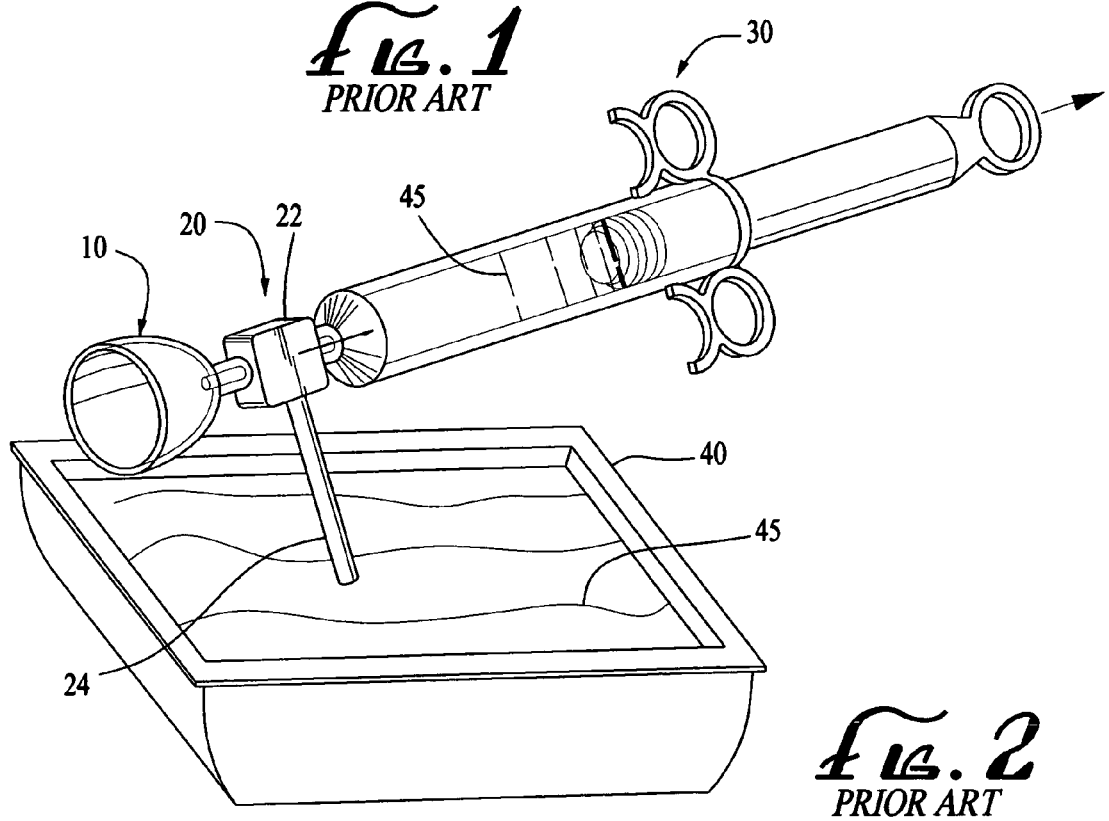
FIG. 2 is a perspective view showing use of the prior art KLENZALAC® wound irrigation system as disclosed in the 1999 Stamler patent.
Figure 3:
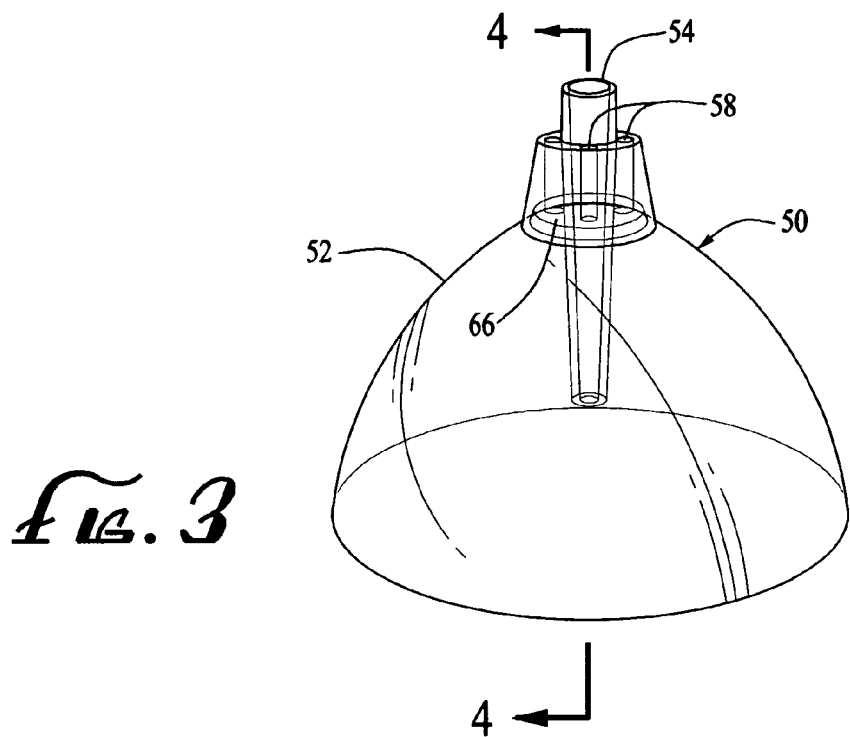
FIG. 3 is a perspective view of the improved splashback shield of the preferred embodiment of the present invention.
Figures 4, 5:
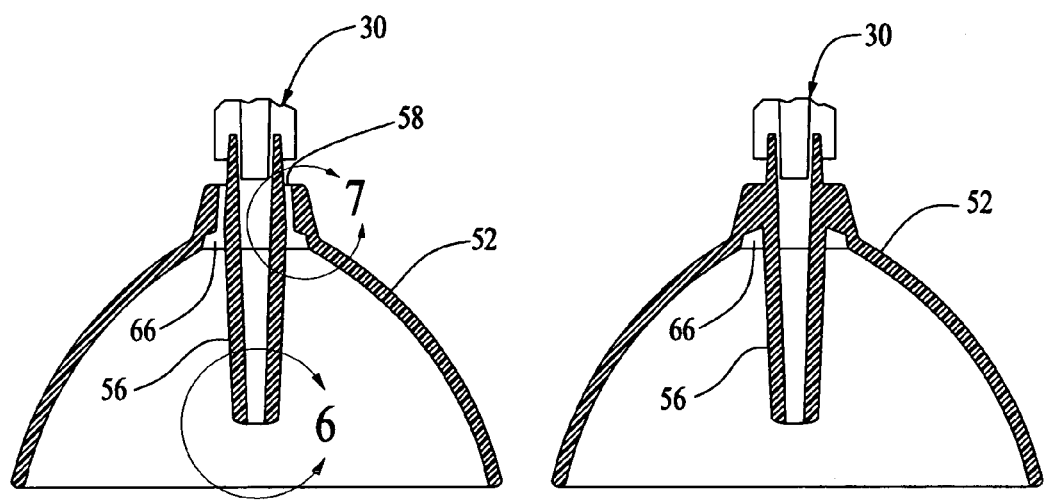
FIG. 4 is a cross-sectional view of the improved splashback shield of the preferred embodiment.
FIG. 5 is another cross-sectional view of the improved splashback shield of the preferred embodiment.

Referring first to FIGS. 3-5, the medical device of the preferred embodiment of the present invention may be described. The splashback shield 50 includes an inverted cup-like shield 52 that is preferably in the shape of a dome, preferably fabricated from a transparent disposable plastic or a glass material. Through the upper end of the shield 52 is a conduit or tunnel 54 that preferably narrows and extends inside the shield 52 to form a nozzle 56.

The splashback shield 50 also includes at least one, e.g. four (4) air vents or passageways 58, preferably grouped around the conduit or tunnel 54 near the top of the shield 52. Note that the apex of the inside of the shield 52 defines a sort of a donut-shaped cavity or cupola-like structure 66, such that small amounts of air which are trapped inside the shield 52 will be compressed into this smaller volume, thus increasing the pressure which encourages escape of said air through said passageways 58. The section view of FIG. 4 is cut through one of the air vents or passageways 58 while the section view of FIG. 5 is cut between the air vents or passageways 58. Optionally although not shown, the cupola 66 may be broken up between the passageways 58 such that each of the passageways 58 has a flared lower end rather than emptying into the shared space of the cupola 66.

Figure 6:
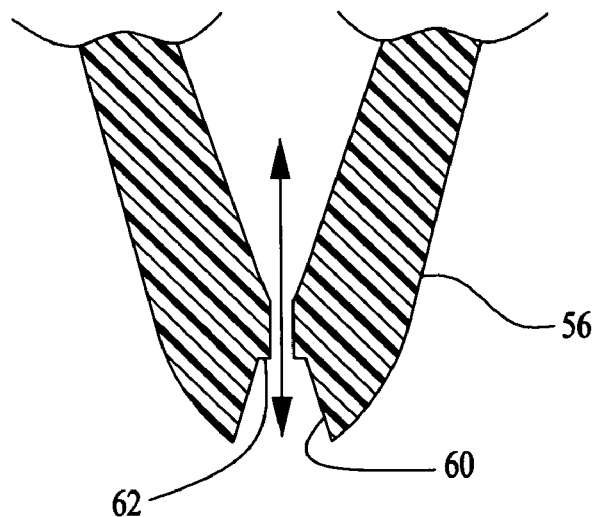
FIG. 6 is an enlarged cross-sectional view showing the configuration of the lower end of the nozzle.

FIGS. 6 shows the details of the preferred structure of the lower or bottom end of the conduit or tunnel 56, which is a flared extension 60 with a small step or flat area 62. This flaring 60 configuration makes drawing up of volumes of irrigant or injectant 45 through the nozzle 56 and into the syringe 30 easier. At the same time the approx. 90 degree step or flat area 62 discourages irrigant or injectant 45 from temporarily clinging to the flared extension 60 of the nozzle 56 during irrigation.

Figure 7:
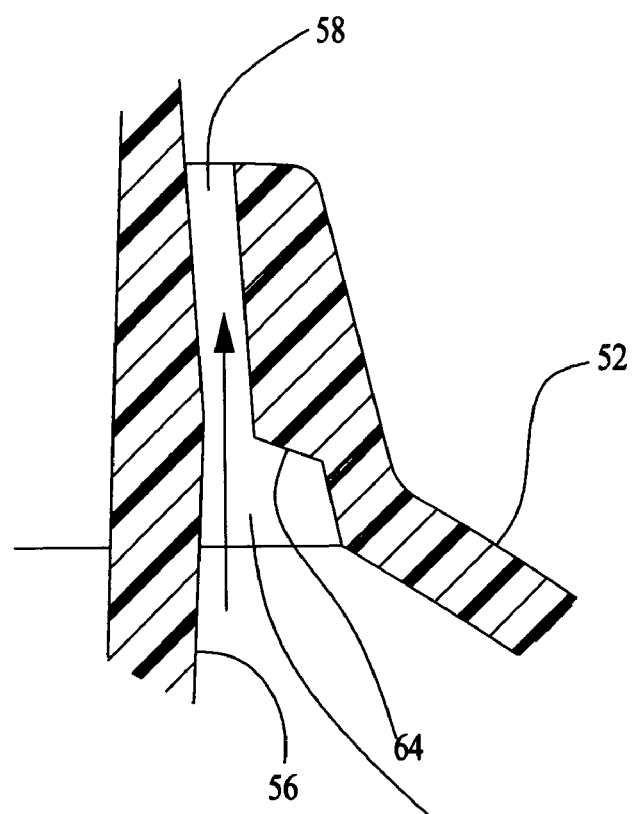
FIG. 7 is an enlarged cross-sectional view showing the configuration of the air vents.

FIG. 7 shows the details of each of the air vents or passageway 58. Each begins at the top of the apical cupola 66 and extends upwardly to a tiny hole at the top. This cupola 66 provides for compression of the air 47, thus increasing the pressure and encouraging escape and release under pressure of the air through the top of the passageway 58. At the same time the elongated passageways 58 tend to contain inside the shield 52 any irrigant or injectant 45 which may accumulate or splash there. The cupola 66 design features as described above cleverly meets the performance objectives of the air vents 58 while maintaining the structural integrity of the shield 52 and actually making the shield 52 easier to manufacture.

Now also referring to FIG. 8, the operation, function and use of the improved splashback shield 50 is discussed, in particular in re-filling the syringe 30 that is the improvement over the prior art 10, 20. The splashback shield 50 is coupled to a syringe 30 and submerged into a basin of irrigant or injectant 45. Recall in using the prior art splashback shield 10 that air 47 would be trapped inside such that it would be drawn into the syringe 30 before the irrigant or injectant 45 (FIG. 6), and hence it was necessary in filling of the syringe 30 to remove the splashback shield 10 and replace it once the syringe 30 was filled.

In utilizing the improved splashback shield 50 it may instead remain attached to the syringe 30, as the nozzle 56 is in the irrigant or injectant 45 and the air 47 is forced out the air vent(s) or passageway(s) 58 or any air 47 remaining in the top of the splashback shield 52 is inconsequential. The plunger 32 is withdrawn which creates a vacuum and pulls the irrigant or injectant 45 into the barrel 34 of the syringe 30. This may be repeated as necessary to conveniently and thoroughly irrigate an average or larger, complex or heavily contaminated wound. Additionally, the nozzle 56 substantially extending into the shield 52 allows irrigant or injectant 45 to be drawn from a very shallow supply of the same.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. An improved splashback shield for attachment to a syringe for wound irrigation comprising:
    a generally transparent and substantially rigid three-dimensional hollow shield having an open lower end and a closed upper end and an inner and outer surface;
    a conduit extending through said outer surface and into said shield in said upper end, said conduit having a top end configured to accept the syringe and generally narrowing as extending downwardly through said inner surface to a bottom end;
    one or more air vent(s) through the upper end of the shield substantially adjacent the conduit,
    whereby when submerging and re-filling the syringe with the shield attached any air trapped inside the shield is able to escape through the air vent(s) rather than being drawn into the syringe.

2. The improved splashback shield of claim 1 wherein the shield is generally dome shaped.

3. The improved splashback shield of claim 1 wherein the conduit extends a substantial distance through the inner surface and into but not past the lower end of the hollow shield.

4. The improved splashback shield of claim 3 wherein the conduit extends downward into the shield below the air vent (s).

5. The improved splashback shield of claim 1 wherein the conduit has a flared bottom end.

6. The improved splashback shield of claim 1 wherein the air vent(s) extend upwardly a substantial distance above the inner surface of the shield.

7. The improved splashback shield of claim 1 wherein the air vent(s) substantially narrow as the air vents extend upwardly.

8. The improved splashback shield of claim 1 wherein the air vent(s) are elongate tubular passageway(s) through the shield.

9. The improved splashback shield of claim 8 wherein the tubular passageway(s) are located within the conduit.

10. An improved splashback shield for attachment to a syringe for wound irrigation comprising:
    a generally transparent and substantially rigid three-dimensional hollow shield having an open lower end and a closed upper end and an inner and outer surface;
    a tubular conduit extending through said outer surface and into said shield in said upper end, said tubular conduit having a top end configured to accept the syringe and generally narrowing as extending downwardly through said inner surface to a bottom end;
    one or more air vent(s) through the upper end of the shield closely near the tubular conduit,
    whereby when submerging and re-filling the syringe with the shield attached any air trapped inside the shield is able to escape through the air vent(s) rather than be drawn into the syringe; and,
    wherein the tubular conduit extends through the inner surface and a substantial distance into the hollow shield below the air vent(s) but not past the lower end of the hollow shield; and,
    wherein the air vent(s) are tubular passageway(s) located within the tubular conduit and extending upwardly a substantial distance above the inner surface of the shield.

11. The improved splashback shield of claim 10 wherein the tubular conduit substantially widens at the bottom end of the tubular conduit.

12. The improved splashback shield of claim 10 wherein the air vent(s) substantially narrow as the air vents extend upwardly.

13. A medical device for containing reflected fluids when an injectant is projected at a wounded area on the human body while at the same time allowing monitoring of the direction and flow of the injectant, the device for use in conjunction with injection means for manually filling and directing the injectant under pressure, comprising:

a transparent, substantially rigid cup-shaped means for covering the wounded area having an upper surface and a lower opening and rim edge placed on or near the wounded area;

tunnel means forming a nozzle for increasing the pressure of the flow of the injectant through the upper surface and down inside the cup-shaped means through a bottom end of the nozzle;

venting means in the upper surface of the cup-shaped means substantially adjacent the tunnel means for allowing air to escape upwardly from inside the cup-shaped means while still containing the injectant;

whereby the injectant is refillable without detaching the cup-shaped means from the injection means.

14. The medical device of claim 13 wherein the nozzle extends a substantial distance downwardly inside the cup-shaped means and below the venting means but not past the rim edge of the cup-shaped means.

15. The medical device of claim 14 wherein the nozzle substantially widens at the bottom end of the nozzle.

16. The medical device of claim 13 wherein the venting means comprises one or more narrow passageway(s) located within the tunnel means.

17. The medical device of claim 16 wherein the passageway(s) substantially further narrow as the passageway(s) extend upwardly.

18. A medical device for containing reflected fluids when an injectant is directed at a wounded area on the human body while at the same time allowing monitoring of the direction and flow of the injectant, the device for use in conjunction with injection means for manually filling and directing the injectant under pressure, comprising:

a transparent, substantially rigid cup-shaped means for covering the wounded area having an upper surface and a lower opening and rim placed on or near the wounded area;

tunnel means forming a nozzle for increasing the pressure of the flow of the injectant through the upper surface and downwardly inside the cup-shaped means through a bottom end of the nozzle;

venting means in the upper surface of the cup-shaped means proximate the tunnel means for allowing air to escape upwardly from inside the cup-shaped means while still containing the injectant;

whereby the injectant is refillable without detaching the cup-shaped means from the injection means; and, wherein the nozzle generally narrows and extends a substantial distance downwardly inside the cup-shaped means and below the venting means; and, wherein the venting means comprises one or more narrow passageway(s) located immediately adjacent the tunnel means.

19. The medical device of claim 18 wherein the nozzle substantially widens at the bottom end of the nozzle.

20. The medical device of claim 18 wherein the venting means substantially further narrows as the venting means extend upwardly.

21. The medical device of claim 18 wherein the nozzle extends not past the rim of the cup-shaped means.

* * * * *